United States Patent
Inagaki et al.

(10) Patent No.: US 11,369,287 B2
(45) Date of Patent: Jun. 28, 2022

(54) STRESS ESTIMATION SYSTEM

(71) Applicant: NTT DOCOMO, INC., Chiyoda-ku (JP)

(72) Inventors: Akiya Inagaki, Chiyoda-ku (JP); Yusuke Fukazawa, Chiyoda-ku (JP); Keiichi Ochiai, Chiyoda-ku (JP)

(73) Assignee: NTT DOCOMO, INC., Chiyoda-ku (JP)

( * ) Notice: Subject to any disclaimer, the term of this patent is extended or adjusted under 35 U.S.C. 154(b) by 336 days.

(21) Appl. No.: 16/462,572

(22) PCT Filed: Apr. 11, 2018

(86) PCT No.: PCT/JP2018/015276
§ 371 (c)(1),
(2) Date: May 21, 2019

(87) PCT Pub. No.: WO2018/190384
PCT Pub. Date: Oct. 18, 2018

(65) Prior Publication Data
US 2020/0060581 A1    Feb. 27, 2020

(30) Foreign Application Priority Data
Apr. 14, 2017  (JP) .............................. JP2017-080771

(51) Int. Cl.
*A61B 5/11* (2006.01)
*A61B 1/005* (2006.01)
(Continued)

(52) U.S. Cl.
CPC ................ *A61B 5/11* (2013.01); *A61B 1/005* (2013.01); *A61B 5/0205* (2013.01);
(Continued)

(58) Field of Classification Search
CPC ... A61B 1/005; A61B 5/0205; A61B 5/02405; A61B 5/02438; A61B 5/11; A61B 5/112; A61B 5/16; A61B 5/486; G01C 22/006
See application file for complete search history.

(56) References Cited

U.S. PATENT DOCUMENTS

| | | | |
|---|---|---|---|
| 2009/0069641 A1* | 3/2009 | Cho ....................... | A61B 5/024 600/300 |
| 2015/0120205 A1* | 4/2015 | Jeon ....................... | A61B 5/015 702/19 |

(Continued)

FOREIGN PATENT DOCUMENTS

| | | |
|---|---|---|
| JP | 2010-213930 A | 9/2010 |
| JP | 2010-234000 A | 10/2010 |

OTHER PUBLICATIONS

International Search Report dated Jul. 10, 2018 in PCT/JP2018/015276 filed on Apr. 11, 2018.
(Continued)

Primary Examiner — Daniel L Cerioni
(74) Attorney, Agent, or Firm — Oblon, McClelland, Maier & Neustadt, L.L.P.

(57) ABSTRACT

A stress estimation system which estimates stress of a user includes a walking speed acquisition unit configured to acquire walking speed information indicating walking speeds of a user in each of the morning and the afternoon at a preset place, an estimation unit configured to calculate a comparison value between the walking speeds in each of the morning and the afternoon indicated by the acquired walking speed information, and to estimate stress of the user based on the calculated comparison value, and an output unit configured to output information in accordance with the estimated stress of the user.

3 Claims, 4 Drawing Sheets

(51) Int. Cl.
*A61B 5/0205* (2006.01)
*A61B 5/024* (2006.01)
*A61B 5/16* (2006.01)
*A61B 5/00* (2006.01)
*G01C 22/00* (2006.01)

(52) U.S. Cl.
CPC ...... *A61B 5/02405* (2013.01); *A61B 5/02438* (2013.01); *A61B 5/16* (2013.01); *A61B 5/486* (2013.01); *G01C 22/006* (2013.01)

(56) References Cited

U.S. PATENT DOCUMENTS

2017/0349097 A1* 12/2017 Nishimura ......... G06K 9/00818
2018/0180442 A1*  6/2018 Uchida ................... G01P 21/02

OTHER PUBLICATIONS

Hayashi, Y. et al., "Fatigue management for seafarers and marine pilots at sea: Possibility of fatigue evaluation by walking velocity", Review of Graduate School of Maritime Sciences, Kobe University, No. 7, Jul. 2010, pp. 21-26, with English Abstract.
International Preliminary Report on Patentability and Written Opinion dated Jul. 10, 2019 in PCT/JP2018/015276 (submitting English translation only), 7 pages.
Japanese Office Action dated Oct. 15, 2019 in Patent Application No. 2019-512560, (with English translation), 7 pages.

* cited by examiner (b)

STRESS ESTIMATION SYSTEM

TECHNICAL FIELD

The present invention relates to a stress estimation system which estimates stress of an estimation target person.

BACKGROUND ART

Conventionally, measuring a state of the heart rate of a stress estimation target person to estimate stress of the estimation target person has been proposed (for example, refer to Patent Literature 1).

CITATION LIST

Patent Literature

Patent Literature 1: Japanese Unexamined Patent Publication No. 2010-234000

SUMMARY OF INVENTION

Technical Problem

It is necessary to attach a heart rate sensor to a stress estimation target person to measure a state of the heart rate of the estimation target person. In addition, continuous stress estimation is required to detect when a stress condition has deteriorated. Therefore, if it is assumed that stress is estimated based on the state of the heart rate, it is necessary to continuously have a heart rate sensor attached to the estimation target person, which imposes a heavy burden on the estimation target person. On the other hand, there is a method of estimating stress by questioning the estimation target person. The method using a questionnaire also imposes a heavy burden on the estimation target person if it is assumed to be performed continuously.

The present invention has been made in view of the above, and an object thereof is to provide a stress estimation system which can estimate stress without imposing a heavy burden on an estimation target person.

Solution to Problem

The inventors of the present invention have found that the estimation of stress can be performed based on walking speeds at different timings in a predetermined place. One embodiment of the present invention is made based on this knowledge. A stress estimation system according to an embodiment of the present invention is a stress estimation system which estimates stress of an estimation target person, and includes a walking speed acquisition unit configured to acquire walking speed information indicating walking speeds of the estimation target person at a first timing and a second timing which is a timing different from the first timing at a preset place, an estimation unit configured to calculate a comparison value between the walking speed at the first timing and the walking speed at the second timing, indicated by the walking speed information acquired by the walking speed acquisition unit, and to estimate stress of the estimation target person based on the calculated comparison value, and an output unit configured to output information in accordance with stress of the estimation target person estimated by the estimation unit.

In the stress estimation system according to an embodiment of the present invention, stress is estimated based on a comparison value calculated from walking speeds. Walking speeds can be detected without imposing a burden on an estimation target person as compared with measurement of a state of the heart rate. Further, there is no need for the estimation target person to provide any types of answers as in a questionnaire. That is, in the stress estimation system according to an embodiment of the present invention, it is possible to estimate stress without imposing a heavy burden on the estimation target person.

Advantageous Effects of Invention

According to one embodiment of the present invention, it is possible to estimate stress without putting a heavy burden on an estimation target person.

DESCRIPTION OF EMBODIMENTS

Figure 1:
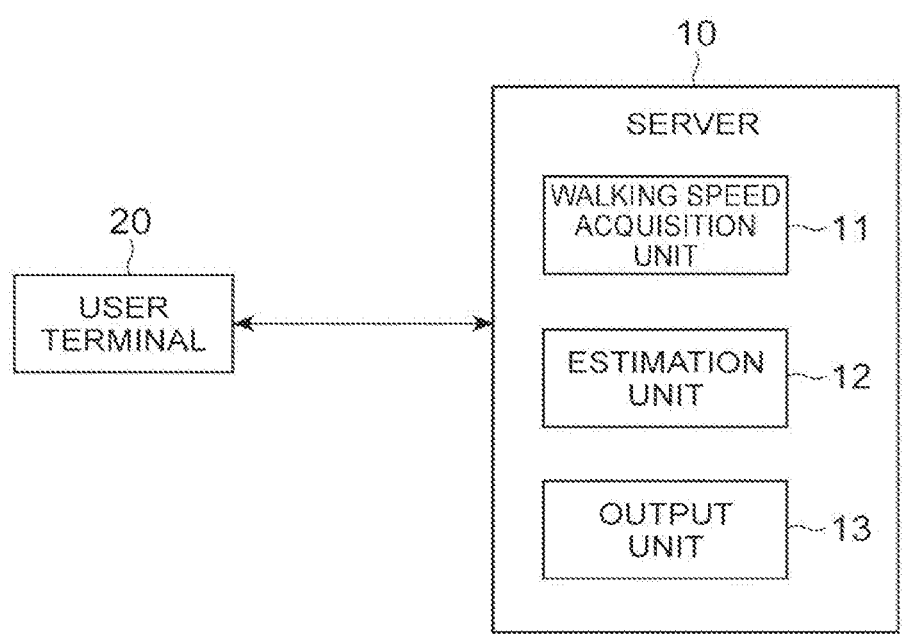
FIG. 1 is a diagram which shows a configuration of a server that is a stress estimation system according to an embodiment of the present invention.

Hereinafter, an embodiment of a stress estimation system according to the present invention will be described in detail with reference to the drawings. Note that the same elements will be denoted by the same reference numerals in description of the drawings, and duplicate description will be omitted.

FIG. 1 shows a server 10 that is a stress estimation system according to the present invention. The server 10 is a system (device) which estimates stress of a user of a user terminal 20 who is a stress estimation target person. In the present embodiment, daily stress of the user will be estimated. Specifically, a degree of stress which the user has accumulated from a certain event will be estimated. For example, a degree of stress at work will be estimated. As described above, one embodiment of the present invention is based on new knowledge found by the inventors that the estimation of stress can be performed according to walking speeds of the user in a predetermined place at different timings. The server 10 performs the estimation of stress of the user based on information transmitted from the user terminal 20.

The user terminal 20 is a device carried and used by the user. The user terminal 20 specifically corresponds to a mobile phone, a smartphone, or the like. The user terminal 20 has a function of performing wireless communication by connecting to a network such as a mobile communication network. The user terminal 20 and the server 10 can communicate with each other via a network, and can transmit or receive information to or from each other.

The user terminal 20 has a positioning function of its own terminal 20 such as a positioning function of the Global Positioning System (GPS). Information indicating a position of the user terminal 20 obtained by the positioning function of the user terminal 20 serves as positional information which indicates a position of the user. The positional information is, for example, information indicating latitude and longitude. In addition, the user terminal 20 has a function of measuring acceleration of its own terminal 20 such as an acceleration sensor. The user terminal 20 periodically (for example, every few seconds or minutes) performs positioning of its own terminal 20 and measurement of the acceleration thereof. The user terminal 20 transmits the positional information of its own terminal 20 and information indicating acceleration thereof, which are obtained by the positioning of its own terminal 20 and the measurement of the acceleration thereof, to the server 10 in association with a time at which the positioning and the measurement are performed. The transmission of the information may also be performed, for example, once a day at a preset time (for example, 0:00).

The user terminal 20, like a normal mobile phone or smartphone, is configured to include hardware such as a central processing unit (CPU), a memory, and a wireless communication module.

Next, a function of the server 10 according to the present embodiment will be described. As shown in FIG. 1, the server 10 is configured to include a walking speed acquisition unit 11, an estimation unit 12, and an output unit 13.

The walking speed acquisition unit 11 is a functional unit which acquires walking speed information indicating the walking speed of the user in a preset place at a first timing and a second timing that is a timing different from the first timing. The walking speed acquisition unit 11 acquires walking speed information indicating the walking speed of the user in the morning of a day as the first timing and the walking speed of the user in the afternoon of the day as the second timing. The walking speed acquisition unit 11 acquires moving state information indicating a physical quantity corresponding to a moving state of the user, determines whether the user is walking based on a physical quantity indicated by the acquired moving state information, and acquires information indicating a moving speed of the user at a timing at which it is determined that the user is walking as a walking speed. The walking speed acquisition unit 11 acquires positional information indicating the position of the user, and acquires walking speed information at a timing at which a position indicated by the acquired positional information is a preset place.

As described above, the walking speed acquisition unit 11 acquires walking speed information which indicates the walking speed of the user in each of the morning and the afternoon of the day in a preset place as the information for estimating the stress of the user. The preset place is, for example, the vicinity of a specific facility such as a user's house. The walking speed acquisition unit 11 acquires information on an average value of walking speeds of the user from 6:00 to 11:00 of the day (a walking speed in a predetermined time zone in the morning), and an average value of walking speeds of the user from 17:00 to 22:00 of the day (a walking speed in a predetermined time zone in the afternoon) in the preset place. The walking speed described above is assumed to be a walking speed at the time of going to work and a walking speed at the time of leaving work. By setting a place in the vicinity of the home and different timings such as morning and afternoon, it is possible to set an appropriate walking speed in view of the estimation of stress at the time of going to work and at the time of leaving work as described above.

Specifically, the walking speed acquisition unit 11 acquires walking speed information as follows. As described above, because the estimation of stress is performed on a daily basis, the walking speed acquisition unit 11 acquires walking speed information on a daily basis. The walking speed acquisition unit 11 receives and acquires positional information and information indicating acceleration transmitted from the user terminal 20. As described above, these types of information are associated with time. Acceleration corresponds to a physical quantity corresponding to the moving state of the user.

The walking speed acquisition unit 11 determines whether the user is walking based on time series acceleration indicated by the received information. The determination can be performed using a conventional technology. In addition, the walking speed acquisition unit 11 determines whether a position indicated by the received positional information is a preset place. For example, the walking speed acquisition unit 11 performs the determination as follows. The walking speed acquisition unit 11 stores the latitude and longitude of the position of home in advance. The walking speed acquisition unit 11 calculates a distance between a latitude and a longitude indicated by the received positional information, that is, the latitude and longitude of the position of the user, and the latitude and longitude of the position of home. The walking speed acquisition unit 11 determines whether the calculated distance is within a preset range, for example, B≤distance≤A. A and B are values which define the vicinity of the user's house, and, for example, A is about 1 km and B is about 200 m. Note that the user's house is not included in the vicinity of the user's house. That is, a walking speed at the user's house is not used for the estimation of stress.

The walking speed acquisition unit 11 extracts information indicating an acceleration at a time at which the user is walking and the position is a preset place based on the determination described above. The walking speed acquisition unit 11 calculates the walking speed of the user in the morning and in the afternoon based on the extracted acceleration to acquire walking speed information. The calculation can be performed using a conventional technology. For example, the walking speed acquisition unit 11 calculates the moving speed by integrating an average acceleration per unit time based on the extracted acceleration at each time in the morning (6:00 to 11:00) and the extracted acceleration at each time in the afternoon (17:00 to 22:00). The walking speed acquisition unit 11 takes an average of the calculated moving speed per unit time in each of the morning and the afternoon, and sets the average of each as the walking speed of the user in the morning and in the afternoon. Note that the walking speed acquisition unit 11 may also calculate the walking speed based on the positional information instead of the acceleration. The walking speed acquisition unit 11 outputs the acquired walking speed information to the estimation unit 12.

The estimation unit 12 is a functional unit which calculates a comparison value between the walking speed at a first timing and the walking speed at a second timing indicated by the walking speed information acquired by the walking speed acquisition unit 11, and estimates the stress of the user based on the calculated comparison value. The estimation unit 12 calculates a value of a ratio between the walking speed at the first timing and the walking speed at the second timing as the comparison value.

Specifically, the estimation unit 12 estimates the stress of the user as follows. The estimation unit 12 inputs walking speed information from the walking speed acquisition unit 11. The estimation unit 12 calculates an index value according to the following equation based on a walking speed indicated by walking speed information as the comparison value described above.

Index value=(walking speed in morning/walking speed in afternoon).

The estimation unit 12 estimates that the stress of the user increases as the calculated index value is larger. The estimation unit 12 estimates (determines) the stress of the user by comparing, for example, the calculated index value and a parameter stored in advance. The estimation unit 12 estimates that, for example, with respect to preset parameters a and b (where a<b), a stress degree is low if the index value is smaller than a, the stress degree is intermediate if the index value is larger than a and smaller than b, and the stress degree is high if the index value is larger than b. The estimation described above is based on knowledge that the walking speed decreases when stress of the day is large, for example, stress due to work of the day is large. The estimation unit 12 outputs information indicating a result of the estimation to the output unit 13.

The output unit 13 is a functional unit which outputs information in accordance with the stress of the user estimated by the estimation unit 12. For example, the output unit 13 transmits and outputs information indicating a degree such as the stress degree to a user terminal. Alternatively, the output unit 13 may output the information to a server or a module that uses the information on the stress of the user. The output unit 13 may output information in accordance with the estimated stress in any form other than the above description. The above is a function of the server 10 according to the present embodiment.

Figure 2:
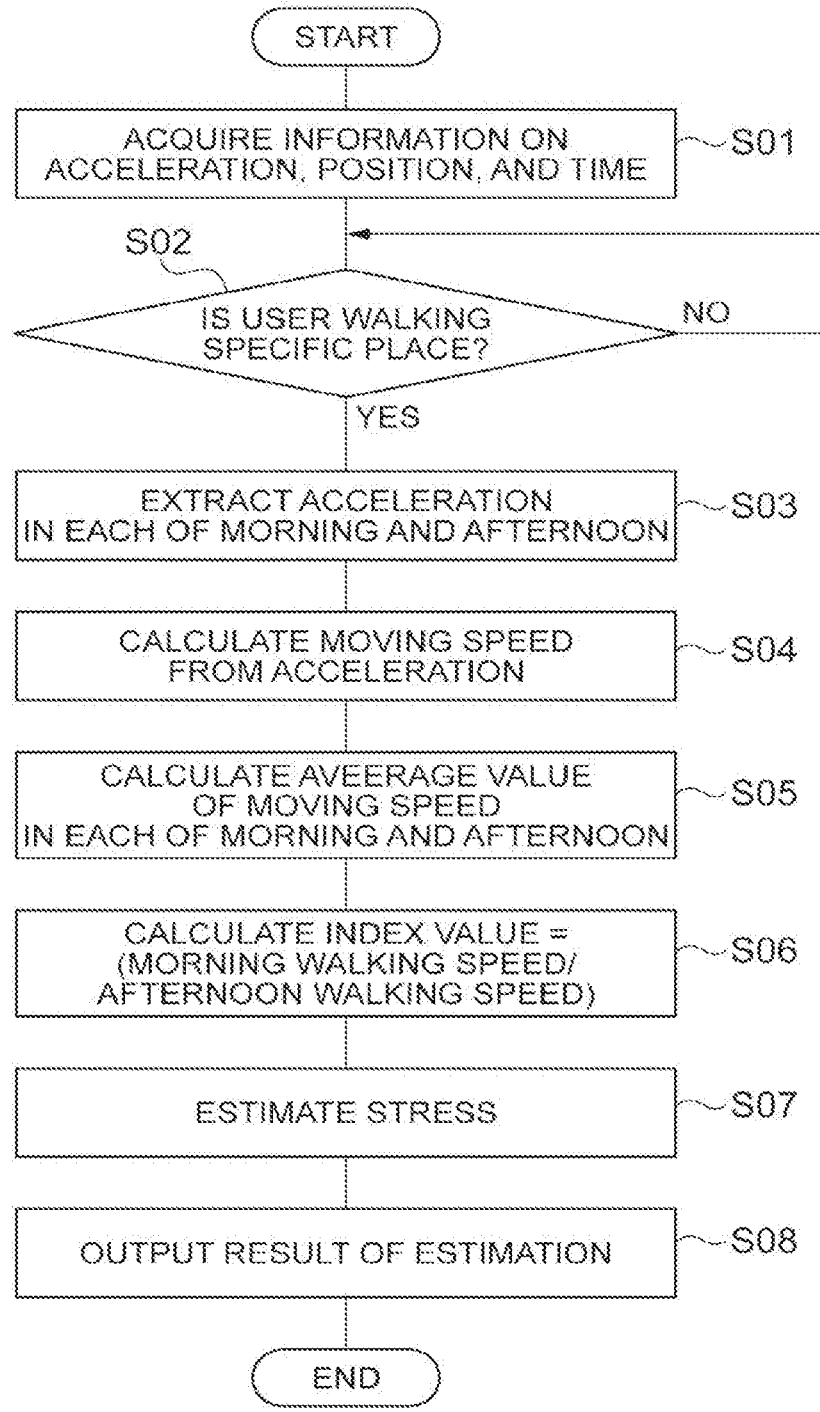
FIG. 2 is a flowchart which shows processing executed by the server that is the stress estimation system according to an embodiment of the present invention.

Next, processing executed by the server 10 (an operation method performed by the server 10) according to the present embodiment will be described using a flowchart of FIG. 2. In the processing, first, the walking speed acquisition unit 11 receives and acquires positional information and information indicating an acceleration, which are transmitted from the user terminal 20 and are associated with time (S01). Subsequently, the walking speed acquisition unit 11 determines whether the information indicates that the user is walking in a specific place, for example, the vicinity of the user's house, based on the received information (S02). The information indicating acceleration in each of the morning and the afternoon is extracted from information which is determined as information indicating that the user is walking in a specific place (Yes in S02) (S03). The above determination is performed for each piece of information, and information which is not determined as information indicating that the user is walking in a specific place (NO in S02) is not extracted.

Subsequently, the walking speed acquisition unit 11 calculates the moving speed per unit time based on an acceleration indicated by the extracted information (S04). Then, the walking speed acquisition unit 11 takes an average of the calculated moving speed per unit time in each of the morning and the afternoon, and sets the average of each as the walking speed of the user in the morning and in the afternoon (S05).

Subsequently, an index value is calculated according to the following equation by the estimation unit 12 (S06).

Index value=(walking speed in morning/walking speed in afternoon)

Subsequently, the estimation unit 12 estimates the stress of the user based on the calculated index value (S07). Then, the output unit 13 outputs information on a result of the estimation (S08). The above is processing executed by the server 10 according to the present embodiment.

As described above, in the present embodiment, the stress is estimated based on the comparison value calculated from the walking speed. Since the walking speed can be acquired according to information obtained from the user terminal 20 carried by the user, it can be detected without imposing a burden on the user as compared with a measurement of a state of the heart rate. In addition, there is no need for the user to provide any types of answers as in a questionnaire. That is, according to the present embodiment, it is possible to estimate stress without imposing a heavy burden on the user. Moreover, according to the present embodiment, it is possible to estimate stress without preparing a heart rate sensor for measuring the state of the heart rate as in the prior art.

In addition, it is possible to appropriately estimate stress of the day, for example, stress at work, through the use of the walking speeds in the morning and in the afternoon of the day as in the present embodiment. However, in an embodiment of the present invention, there is no need to use the walking speeds in the morning and in the afternoon, and walking speeds at different timings may be used.

Moreover, as in the present embodiment, it may be determined whether the user is walking based on the acceleration of the user terminal 20. According to this configuration, it is possible to appropriately acquire walking speed information and to appropriately execute one embodiment of the present invention. Note that there is no need to necessarily use the acceleration to determine whether the user is walking, and any type of moving state information other than the acceleration by which it can be determined whether the user is walking may also be used. In addition, when it can be assumed that the user is walking during movement or when it is determined that the user is walking using another device, it is not necessary to perform the above determination of walking in the server 10.

In addition, as in the present embodiment, it may be determined that the user is positioned at a preset place such as the vicinity of the user's house based on the positional information. According to this configuration, it is possible to appropriately acquire walking speed information at a preset place of the user, and to appropriately execute one embodiment of the present invention. Moreover, when it is determined that the user is at a preset place using another device, there is no need to perform the above determination in the server 10.

In addition, like the index value described above, a value of a walking speed ratio may also be used as an index value (a comparison value). According to this configuration, it is possible to estimate the stress of the user appropriately and reliably. However, there is no need to necessarily use the value of the ratio, and a value other than the value of the ratio may also be used as a comparison value.

In addition, the user terminal 20 may also include a part of the function of the server 10 in the present embodiment. That is, the user terminal 20 may also be included in the stress estimation system according to an embodiment of the present invention. For example, the determination on whether the user is walking and the determination on whether the position of the user is a preset place (the vicinity of the user's house as described above) may be performed by the user terminal 20. In addition, the user terminal 20 may also include all of the functions of the server 10 in the present embodiment. That is, the user terminal 20 may be the stress estimation system according to an embodiment of the present invention.

Figure 3:
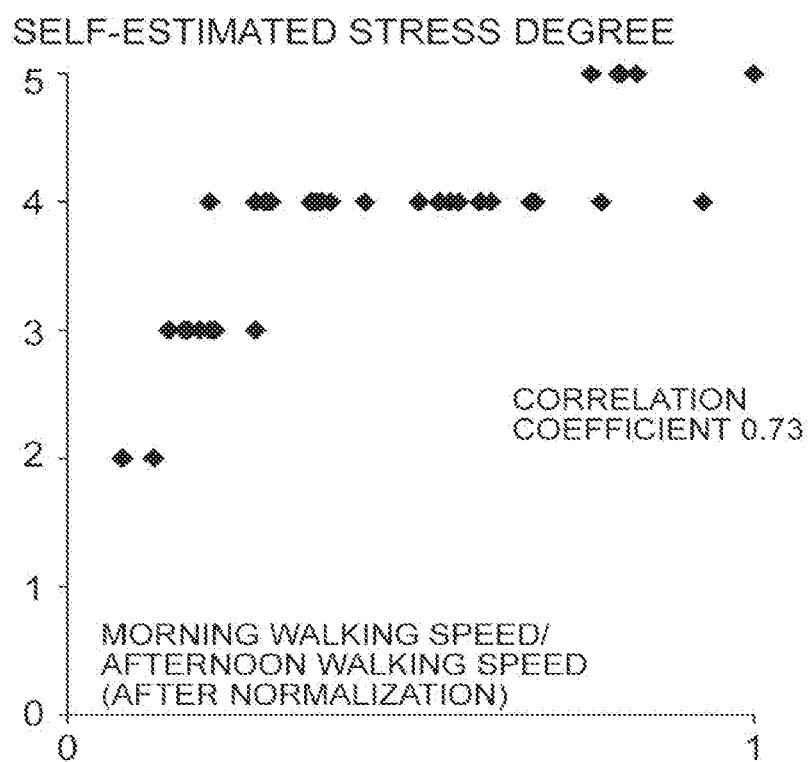
FIG. 3 is a scatter diagram of an index value used for estimation of stress in the present embodiment and a self-estimated stress degree.
Figure 3:
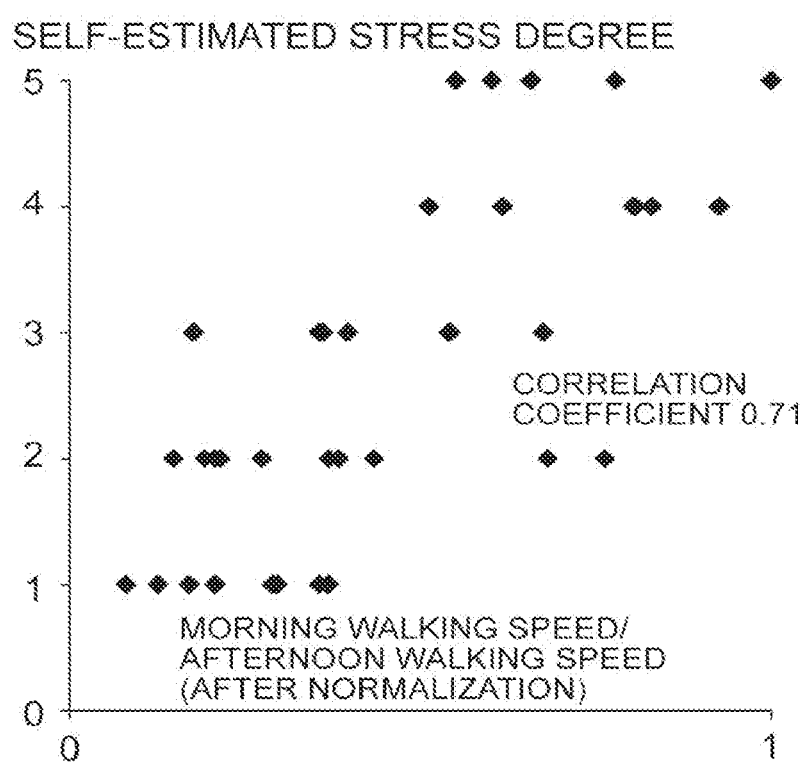

Here, data for supporting stress estimation according to an embodiment of the present invention is shown. FIG. 3 shows scatter diagrams of index values used for the estimation of stress in the present embodiment and a self-estimated stress degree. The scatter diagrams of FIGS. 3 (a) and 3 (b) are scatter diagrams for different users.

A horizontal axis of the scatter diagrams is an index value used for the estimation of stress in the present embodiment, that is, a value of (walking speed in morning/walking speed in afternoon). Note that, in these scatter diagrams, the index values are normalized to values between 0 and 1. A vertical axis of the scatter diagrams is obtained by evaluating the degree of stress self-evaluated by the user in five steps of 1 to 5 on the day related to the index value. It is indicated that the stress of the user increases as a value of the stress degree is larger. In the scatter diagrams of FIGS. 3 (a) and (b), the correlation coefficients are 0.73 and 0.71, respectively. This result is consistent with the present embodiment in which it is estimated that the stress of the user increases as the index value is larger.

Note that a block diagram used in the description of the embodiment described above shows a block of a functional unit. These functional blocks (configuration units) are implemented by any combination of hardware and/or software. In addition, an implementation unit of each functional block is not particularly limited. That is, each functional block may be implemented by one physically and/or logically combined device, and may also be implemented by directly and/or indirectly (for example, by wire and/or wirelessly) connecting two or more devices which are physically and/or logically separated.

Figure 4:
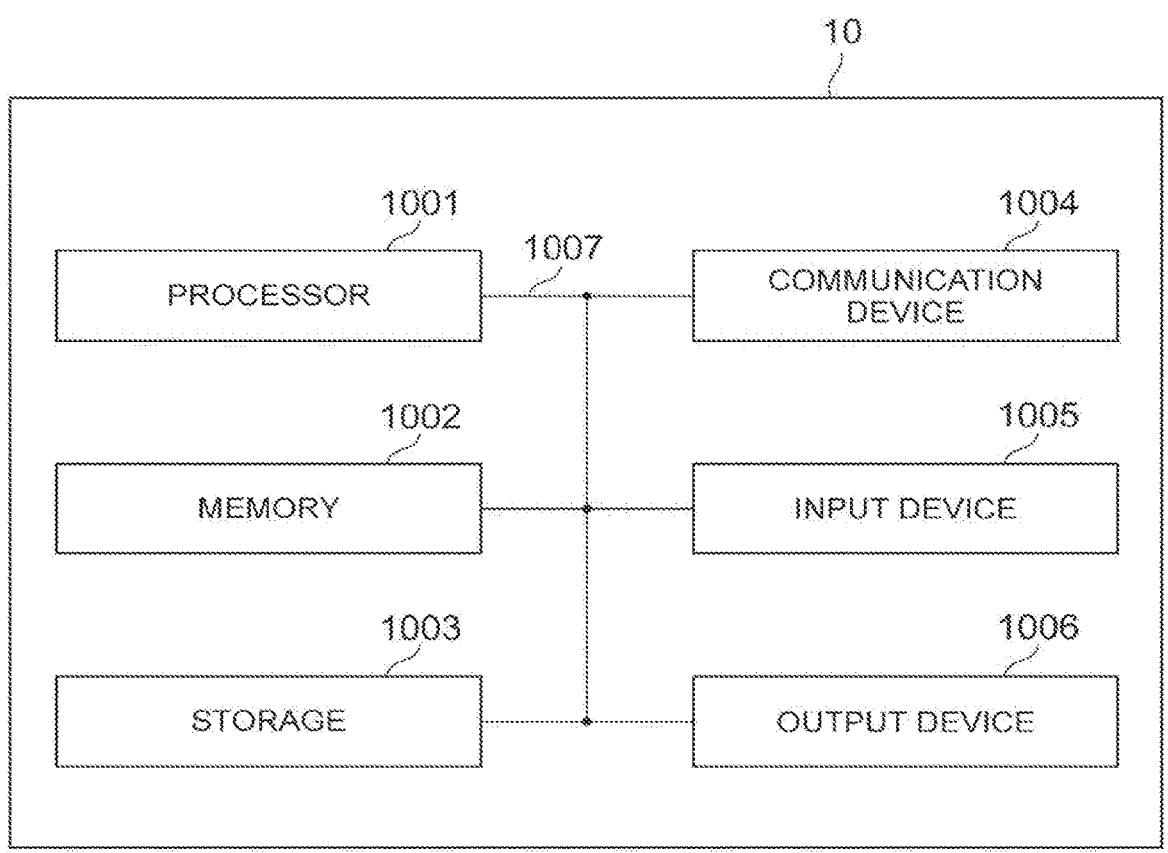
FIG. 4 is a diagram which shows a hardware configuration of the server that is the stress estimation system according to an embodiment of the present invention.

For example, the server 10 according to an embodiment of the present invention may function as a computer that performs the processing of the server 10 of the present embodiment. FIG. 4 is a diagram which shows an example of the hardware configuration of the server 10 according to the present embodiment. The server 10 described above may be physically configured as a computer device including a processor 1001, a memory 1002, a storage 1003, a communication device 1004, an input device 1005, an output device 1006, a bus 1007, and the like.

Note that the term "device" can be interpreted as a circuit, a device, a unit, or the like in the following description. A hardware configuration of the server 10 may be configured to include one or more of each unit shown in drawings, and may also be configured not to include some devices.

Each function in the server 10 is implemented by the processor 1001 performing calculation by causing predetermined software (a program) on hardware such as the processor 1001 and the memory 1002 to be read, and by controlling communication by the communication device 1004 and reading and/or writing of data in the memory 1002 and the storage 1003.

The processor 1001 operates, for example, an operating system to control an entire computer. The processor 1001 may be configured by a central processing unit (CPU) including an interface with a peripheral device, a control device, an arithmetic device, a register, and the like. For example, respective functional units 11 to 13 of the server 10 may be implemented to include the processor 1001.

In addition, the processor 1001 reads a program (a program code), a software module, and data from the storage 1003 and/or the communication device 1004 to the memory 1002, and executes various types of processing according to these. As the program, a program which causes a computer to execute at least a part of the operation described in the embodiment described above is used. For example, the respective functional units 11 to 13 of the server 10 may be stored in the memory 1002, may be implemented by a control program operating using the processor 1001, and other functional blocks may be implemented similarly. It has been described that the various types of processing described above are executed by one processor 1001, but they may be executed simultaneously or sequentially by two or more processors 1001. The processor 1001 may be mounted by one or more chips. Note that the program may be transmitted from a network via a telecommunication line.

The memory 1002 is a computer-readable recording medium, and may be configured to include, for example, at least one of a read only memory (ROM), an erasable programmable ROM (EPROM), an electrically erasable programmable ROM (EEPROM), a random access memory (RAM), and the like. The memory 1002 may be called a register, a cache, a main memory (main storage device), or the like. The memory 1002 can save a program (a program code), a software module, and the like which can be executed to implement a method according to an embodiment of the present invention.

The storage 1003 is a computer-readable recording medium, and may be configured to include, for example, at least one of an optical disc such as a compact disc ROM (CD-ROM), a hard disk drive, a flexible disk, a magneto-optical disc (for example, a compact disc, a digital versatile disk, a Blu-ray (registered trademark) disk), a smart card, a flash memory (for example, a card, a stick, a key drive), a floppy (registered trademark) disk, a magnetic strip, and the like. The storage 1003 may be called an auxiliary storage device. The storage medium described above may be, for example, a database including the memory 1002 and/or the storage 1003, a server, or any other suitable medium.

The communication device 1004 is hardware (a transmission and reception device) for performing communication between computers via a wired and/or wireless network, and refers to, for example, a network device, a network controller, a network card, a communication module, and the like. For example, the respective functional units 11 to 13 of the server 10 described above may be implemented to include the communication device 1004.

The input device 1005 is an input device (for example, a keyboard, a mouse, a microphone, a switch, a button, a sensor, or the like) which receives an input from the outside. The output device 1006 is an output device (for example, a display, a speaker, an LED lamp, or the like) which performs an output to the outside. Note that the input device 1005 and the output device 1006 may be an integrated constituent (for example, a touch panel).

In addition, respective devices such as the processor 1001, the memory 1002, and the like are connected by the bus 1007 for communicating information. The bus 1007 may be configured as a single bus or may be configured as different buses among devices.

In addition, the server 10 may be configured to include hardware such as a micro-processor, a digital signal processor (DSP), an application specific integrated circuit (ASIC), a programmable logic device (PLD), or a field programmable gate array (FPGA), and some or all of respective functional blocks may be implemented by the hardware. For example, the processor 1001 may be implemented by at least one of these pieces of hardware.

As described above, although the present embodiment has been described in detail, it is clear for those skilled in the art that the present embodiment is not limited to the embodiment described in this specification. The present embodiment can be implemented as a modification and a change mode without deviating from the gist and scope of the present invention defined by description of claims. Therefore, the description of the present specification is for the purpose of illustration and does not have any limited meaning with respect to the present embodiment.

Processing procedures, sequences, flowcharts, and the like of the respective aspects and embodiments described in the present specification may be switched in order as long as there is no contradiction. For example, for the method described in the present specification, elements of various steps are presented in an exemplified order, and the present invention is not limited to a presented specific order.

The input and output information may be saved in a specific place (for example, a memory), or may be managed by a management table. The input and output information and the like can be overwritten, updated, or added. The output information and the like may be deleted. The input information and the like may be transmitted to another device.

The determination may be performed by a value (0 or 1) represented by one bit, may be performed by a Boolean value (Boolean: true or false), and may be performed by comparison with a numerical value (for example, comparison with a predetermined value).

Each aspect or embodiment described in the present specification may be used alone, may be used in combination, and may also be switched and used along with execution. In addition, notification of predetermined information (for example, notification of "it is X") is not limited to being performed in an explicit manner, and may be performed in an implicit manner (for example, not notification of the predetermined information).

Regardless of whether the software is called software, firmware, middleware, a micro-code, or a hardware description language, or whether it is called by other names, the software needs to be interpreted broadly to mean an instruction, an instruction set, a code, a code segment, a program code, a program, a sub-program, a software module, an application, a software application, a software package, a routine, a subroutine, an object, an executable file, an execution thread, a procedure, a function, and the like.

In addition, software, instructions, and the like may be transmitted or received via a transmission medium. For example, when the software is transmitted from a website, a server, or other remote sources using wired technologies such as a coaxial cable, a fiber optic cable, a twisted pair, and a digital subscriber line (DSL), and/or wireless technologies such as infrared, wireless, and microwave, these wired and wireless technologies are included within a definition of the transmission medium.

The information, signals, and the like described in the present specification may be represented using any one of various different technologies. For example, the data, instructions, commands, information, signals, bits, symbols, chips, and the like throughout the above description may be represented by voltages, currents, electromagnetic waves, magnetic fields or magnetic particles, light fields or photons, or any combination thereof.

Note that the terms described in the present specification and/or the terms necessary for the understanding of the present specification may be replaced with terms having the same or similar meanings.

The terms referred to as "system" and "network" used in the present specification are interchangeably used.

Moreover, the information, parameters, and the like described in the present specification may be represented by absolute values, may also be represented by relative values from a predetermined value, or may be represented by different corresponding information.

The names used for the parameters described above are not limited in any way. Furthermore, formulas and the like using these parameters may differ from those explicitly disclosed in the present specification.

A mobile communication terminal may be called a subscriber station, a mobile unit, a subscriber unit, a wireless unit, a remote unit, a mobile device, a wireless device, a wireless communication device, a remote device, a mobile subscriber station, an access terminal, a mobile terminal, a wireless terminal, a remote terminal, a handset, a user agent, a mobile client, a client, or some other suitable terms by those skilled in the art.

The terms of "determining" and "determining" used in the present specification may include many different types of operations. "Determining" and "determining" may include consideration as "determining" and "determining" of a thing subjected to calculating, computing, processing, deriving, investigating, looking up (for example, looking up with a table, a database, or another data structure), or ascertaining. In addition, "determining" and "determining" may include consideration as "determining" and "determining" of a thing subjected to receiving (for example, receiving information), transmitting (for example, transmitting information), inputting, outputting, or accessing (for example, accessing data in a memory). In addition, "determining" and "determining" may include consideration as "determining" and "determining" of a thing subjected to resolving, selecting, choosing, establishing, comparing, or the like. That is, "determining" and "determining" may include consideration as "determining" and "determining" of any operation.

The phrase of "based on" used in the present specification does not mean "based only on" unless separately stated. In other words, the phrase "based on" means both "based only on" and "based at least on."

In the case of using a designation such as "first" or "second" in the present specification, any reference to the element does not generally limit the quantity or order of those elements. These designations may be used in the present specification as a convenient way of distinguishing between two or more elements. Therefore, reference to the first and the second elements does not mean that only two elements can be adopted there, or that the first element has to precede the second element in any way.

As long as "include," "including," and modifications of these are used in the present specification or claims, these terms, like the term of "comprising", are intended to be inclusive. Furthermore, the term of "or" used in the present specification or in the claims is intended not to be an exclusive OR.

In the present specification, a plurality of devices are included unless there is a device clearly existing only one in a context or technically. Throughout the present disclosure, unless the context clearly indicates a singular device, a plurality of devices are included.

REFERENCE SIGNS LIST

10 Server
11 Walking speed acquisition unit
12 Estimation unit
13 Output unit
1001 Processor
1002 Memory
1003 Storage
1004 Communication device
1005 Input device
1006 Output device 1007 Bus
20 User terminal

The invention claimed is:

1. A stress estimation system which estimates stress of an estimation target person comprising:
   a global positioning system (GPS) device configured to detect a position of a user terminal of the user; and
   circuitry configured to
      acquire walking speed information, based on detecting multiple positions of the user terminal by the GPS device at different times, indicating walking speeds of the estimation target person at a first timing and a second timing which is a timing different from the first timing at a preset place;
      calculate a ratio of the walking speed at the first timing and the walking speed at the second timing;
      estimate stress of the estimation target person based on the calculated ratio; and
      output information in accordance with stress of the estimation target person estimated,
   wherein the circuitry acquires positional information indicating a position of the estimation target person, determine whether the position indicated by the acquired positional information is the preset place using information indicating the preset place stored in advance, and acquire the walking speed information when the position is determined to be the preset place, and
   the circuitry acquires the walking speed information indicating a walking speed of the estimation target person in the morning of a day as the first timing, and a walking speed of the estimation target person in the afternoon of the day as the second timing, and the circuitry estimates a high degree of stress for the estimation target person when the calculated ratio is higher than a preset parameter.

2. The stress estimation system according to claim 1, wherein the circuitry acquires moving state information indicating a physical quantity corresponding to a moving state of the estimation target person, determines whether the estimation target person is walking based on the physical quantity indicated by the acquired moving state information, and acquires information indicating a moving speed of the estimation target person, as the walking speed at either the first timing or the second timing at which it is determined that the estimation target person is walking.

3. A method implemented by stress estimation system which estimates stress of an estimation target person, the method comprising:
   detecting, by a global positioning system (GPS) device, a position of a user terminal of the user;
   acquiring, by circuitry, walking speed information, based on detecting multiple positions of the user terminal by the GPS device at different times, indicating walking speeds of the estimation target person at a first timing and a second timing which is a timing different from the first timing at a preset place;
   calculating, by the circuitry, a ratio of the walking speed at the first timing and the walking speed at the second timing; and
   estimating, by the circuitry, stress of the estimation target person based on the calculated ratio; and
   outputting, by the circuitry, information in accordance with stress of the estimation target person estimated,
   wherein the method includes acquiring positional information indicating a position of the estimation target person, determining whether the position indicated by the acquired positional information is the preset place using information indicating the preset place stored in advance, and acquiring the walking speed information when the position is determined to be the preset place, and
   the method further includes acquiring the walking speed information indicating a walking speed of the estimation target person in the morning of a day as the first timing, and a walking speed of the estimation target person in the afternoon of the day as the second timing, and estimating a high degree of stress for the estimation target person when the calculated ratio is higher than a preset parameter.

\* \* \* \* \*